US007260242B2

(12) United States Patent
Viggh

(10) Patent No.: US 7,260,242 B2
(45) Date of Patent: Aug. 21, 2007

(54) SPATIAL SURFACE PRIOR INFORMATION REFLECTANCE ESTIMATION (SPIRE) ALGORITHMS

(75) Inventor: Herbert E. M. Viggh, Boxborough, MA (US)

(73) Assignee: United States of America as represented by the Secretary of the Air Force, Washington, DC (US)

( * ) Notice: Subject to any disclaimer, the term of this patent is extended or adjusted under 35 U.S.C. 154(b) by 854 days.

(21) Appl. No.: 10/642,809

(22) Filed: Aug. 15, 2003

(65) Prior Publication Data
US 2005/0036661 A1   Feb. 17, 2005

(51) Int. Cl.
*G06K 9/40* (2006.01)
(52) U.S. Cl. ...................................... 382/103; 382/275
(58) Field of Classification Search ................. 382/103, 382/108, 274, 275, 276, 280, 281
See application file for complete search history.

(56) References Cited

U.S. PATENT DOCUMENTS

| 5,371,542 A | * | 12/1994 | Pauli et al. ................. 348/262 |
| 5,448,052 A | * | 9/1995 | Taylor et al. ............. 250/201.9 |
| 5,841,911 A | * | 11/1998 | Kopeika et al. ............ 382/254 |
| 2004/0124335 A1 | * | 7/2004 | Cicchiello et al. ....... 250/201.9 |
| 2004/0153284 A1 | * | 8/2004 | Bernstein et al. ............ 702/178 |
| 2006/0291693 A1 | * | 12/2006 | Olson et al. ................. 382/103 |

\* cited by examiner

*Primary Examiner*—Andrew W. Johns
(74) *Attorney, Agent, or Firm*—AFMC LO/JAZ; William G. Auton; Jeffrey R. Moore

(57) ABSTRACT

A new class of algorithms has been developed to estimate spectral reflectance in remote sensing imagery. These algorithms are called Surface Prior Information Reflectance Estimation (SPIRE) algorithms and estimate surface spectral reflectance using prior spatial and spectral information about the surface reflectance. This paper describes SPIRE algorithms that employ spatial processing of single channel data to estimate local changes in spectral reflectance under spatially and spectrally varying multiplicative and additive noise caused by variations in illumination and atmospheric effects. Rather than modeling the physics of the atmosphere and illumination (using a physics-based code such as ATREM), or using ground truth spectra at known locations to compensate for these effects (using the Empirical Line Method), prior information about the low spatial frequency content of the scene in each spectral channel is used instead. HYDICE VNIR-SWIR hyperspectral data were used to compare the performance of SPIRE, ATREM, and ELM atmospheric compensation algorithms. The Spatial SPIRE algorithm performance was found to be nearly identical to the ELM ground-truth based results, while Spatial SPIRE performed better than ATREM overall, and significantly better under high clouds and haze.

4 Claims, 10 Drawing Sheets

SPATIAL SURFACE PRIOR INFORMATION REFLECTANCE ESTIMATION (SPIRE) ALGORITHMS

STATEMENT OF GOVERNMENT INTEREST

The invention described herein may be manufactured and used by or for the Government for governmental purposes without the payment of any royalty thereon.

BACKGROUND OF THE INVENTION

The present invention relates generally to spectroscopy and more specifically to a new class of algorithms to estimate spectral reflectance in remote sensing imagery. These algorithms are called Surface Prior Information Reflectance Estimation (SPIRE) algorithms and estimate surface spectral reflectance using prior spatial and spectral information about the surface reflectance.

A fundamental problem in many imaging and remote sensing problems is the estimation of the surface reflectance of objects and materials in an imaged scene. The measured scene radiance is generated by complex physical interactions between the source illumination, material surfaces, and the intervening atmosphere. Changes in atmospheric conditions and the relative positions of the sensor, surface, and illumination source introduce variations between images of the same scene collected at different times. These changing illumination and backscatter effects must be compensated in order to estimate the surface reflectance of the scene. In applications where changes in surface reflectance are to be estimated, the multiplicative effects of varying illumination and the additive effects of backscatter, both of which can be viewed as noise, must be separated from the desired changes in surface reflectance. This is usually referred to as the atmospheric compensation problem or atmospheric correction.

This paper addresses the specific problem of estimating the spectral reflectance of local changes in a scene under spatially and spectrally varying multiplicative and additive noise. Applications for such algorithms include environmental assessment, land use, urban growth, and management of renewable natural resources. The detection and measurement of such changes requires the accurate estimation of the surface reflectance over the entire scene so that changes can be detected in comparison to a prior reflectance image. Accurate estimation of the spectral reflectance of the changes themselves is needed as well to correctly measure, identify, and classify them.

Existing atmospheric compensation algorithms typically work well only under certain restrictive conditions such as having pixels of known reflectance and location, or clear, cloud-free conditions. They also often require input from an analyst and guided iteration to achieve the best results. For operational purposes, atmospheric compensation algorithms often need to work without analyst guidance or reliance upon known reflectances, and need to handle images collected under a broad range of atmospheric conditions, including overcast or cloudy skies. Also, many applications rely on airborne sensors that may be flown under overcast skies.

The algorithms developed in this paper are applicable to single channel, multispectral and hyperspectral problems that meet the following conditions. First, a good prior estimate of the reflectance must exist. This prior would typically be acquired under conditions appropriate for use of the existing atmospheric compensation algorithms. In applications where only relative changes are needed, the SPIRE algorithms themselves can be used to generate the prior. The second condition is that any changes in the scene following the prior image collection are spatially limited compared to the size of the image. Examples include moving vehicles and the construction of new buildings, roads, and waterways. The third condition is that the multiplicative and additive illumination effects should vary smoothly across the scene. This applies to nearly all overcast and haze conditions that do not produce sharp cloud shadows, and to conditions where no extensive shadowing from terrain and objects is present. Finally, there should be no opaque clouds between the sensor and the ground. Under these circumstances images can be collected under a wide variety of illumination conditions and can be processed to estimate reflectance. SPIRE extends beyond existing algorithms the conditions under which atmospheric compensation can be performed.

Historically, the two main techniques for performing atmospheric compensation are the Empirical Line Method (ELM) and the atmospheric physics-based approach. The ELM (Kruse, et. al., 1990, *ENVI User's Guide*, 1997) uses prior ground truth spectra for one or more pixels at known locations in the image to compensate for changes in illumination and atmospheric conditions. These corrections for the "truth" pixels are then applied to the rest of the pixels in the image. The ELM typically estimates well the surface reflectance of the image. However, if there are spatially varying effects over parts of the image where there are no ground truth points, then the estimates in these areas will be worse. In other words, the atmospheric compensation will be best near the ground truth points, and potentially worse elsewhere. The ELM also suffers where the images do not have well calibrated test panels for which ground truth spectra are available. Even if a prior reflectance image exists which could provide "truth" spectra, the random location of changes in subsequent images makes it difficult to select automatically the spectra to use.

In the physics-based approach, models of the atmosphere and radiation transfer physics are used to estimate the effects of the atmosphere on the sensed scene and then to compensate for them in order to recover surface reflectance. These techniques do not need information regarding the surface reflectance, but they do require information regarding the state of the atmosphere so that its effect on solar radiation can be modeled. Some atmospheric state information is extracted from the hyperspectral data itself. For example, the effects of water vapor are estimated by using the ratios of certain channels near and in water vapor absorption bands (Kaufman and Sendra 1988, Kaufman and Gao 1992). Typically, other information such as the type of aerosol model to use and the visibility must be input by an analyst. Whether or not all needed atmospheric state information can be extracted from hyperspectral data is an on-going current area of research. Most atmospheric physics-based codes assume a clear, cloudless day, and their performance degrades when there are overcast clouds or haze.

Two commonly used physics-based codes are discussed here: the ATmospheric REMoval (ATREM) (ATREM User's Guide 1997) program, and Air Force Research Lab (AFRL)/MODTRAN code (Adler-Golden, et. al., 1998). ATREM uses the 6S (Second Simulation of the Satellite Signal in the Solar Spectrum) (Vermote 1997) radiative transfer code. The AFRL code uses the MODTRAN (Berk, et. al., 1998) radiative transfer code. MODTRAN was patented by the U.S. Air Force in U.S. Pat. No. 5,884,226, the disclosure of which is incorporated herein by reference.

SUMMARY OF THE INVENTION

The present invention includes the application of a new class of algorithms has been developed to estimate spectral reflectance in remote sensing imagery. These algorithms are called Surface Prior Information Reflectance Estimation (SPIRE) algorithms and estimate surface spectral reflectance using prior spatial and spectral information about the surface reflectance. This description describes SPIRE algorithms that employ spatial processing of single channel data to estimate local changes in spectral reflectance under spatially and spectrally varying multiplicative and additive noise caused by variations in illumination and atmospheric effects. Rather than modeling the physics of the atmosphere and illumination (using a physics-based code such as ATREM), or using ground truth spectra at known locations to compensate for these effects (using the Empirical Line Method), prior information about the low spatial frequency content of the scene in each spectral channel is used instead. HYDICE VNIR-SWIR hyperspectral data were used to compare the performance of SPIRE, ATREM, and ELM atmospheric compensation algorithms. The Spatial SPIRE algorithm performance was found to be nearly identical to the ELM ground-truth based results, while Spatial SPIRE performed better than ATREM overall, and significantly better under high clouds and haze.

DESCRIPTION OF THE DRAWINGS

FIG. 7. Classification results for the Run 13(a) and Run 06(b) estimated reflectance cubes from ELM, ATREM, and Spatial SPIRE algorithms. Run 13 and the training data from Run 07 were collected on the same day under similar illumination conditions as. The Run 06 data occurred on a different day with different illumination conditions.

DESCRIPTION OF THE PREFERRED EMBODIMENT

Figure 1:
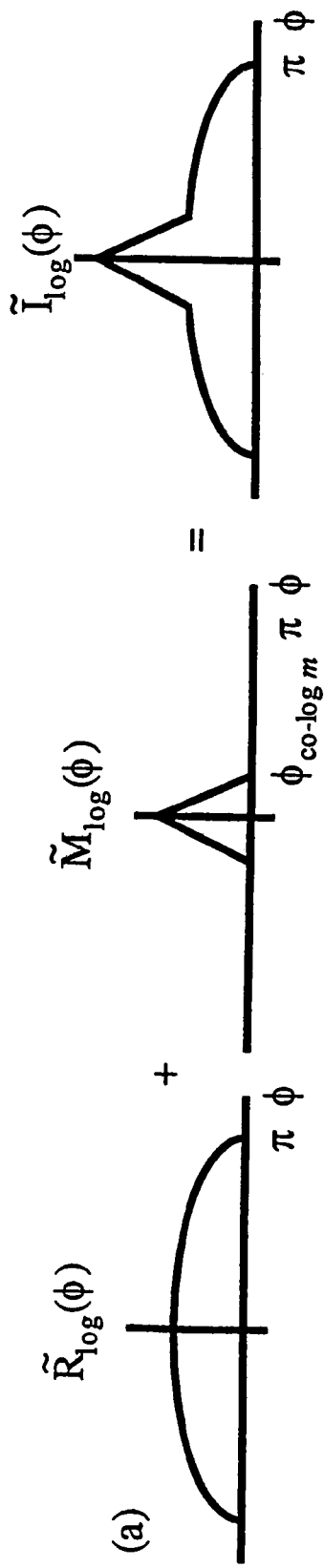
FIGS. 1a-1c are illustrations of multiplicative-noise-only problem and algorithm depicted in the log spatial frequency domain. (a) log image spectrum $I_{log}^{\%}(\phi)$ containing multiplicative noise $M_{log}^{\%}(\phi)$. (b) $I_{log}^{\%}(\phi)$ after noise is excised. (c) log surface reflectivity spectrum estimate $\hat{R}_{log}^{\%}(\phi)$ after the prior low frequencies are inserted.
Figure 1:
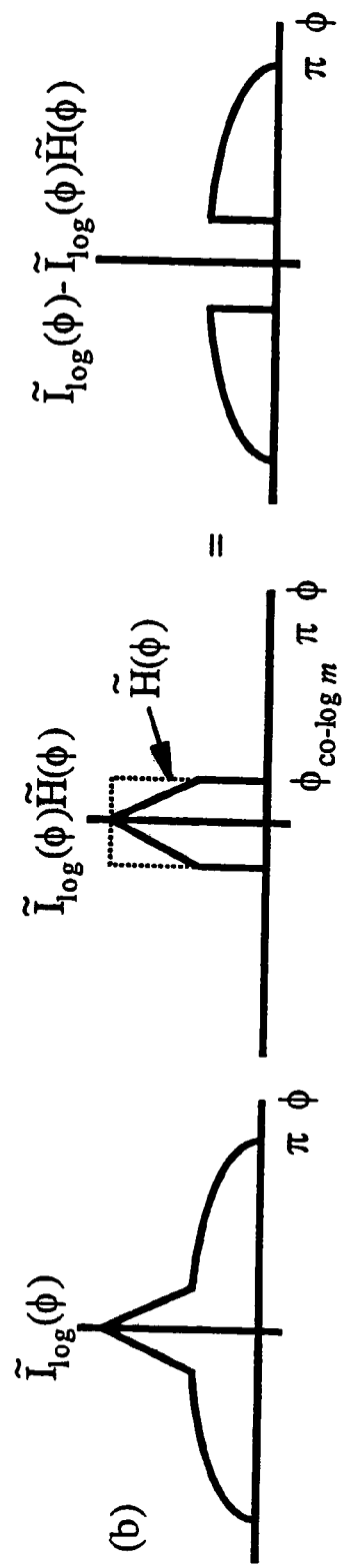
Figure 1:
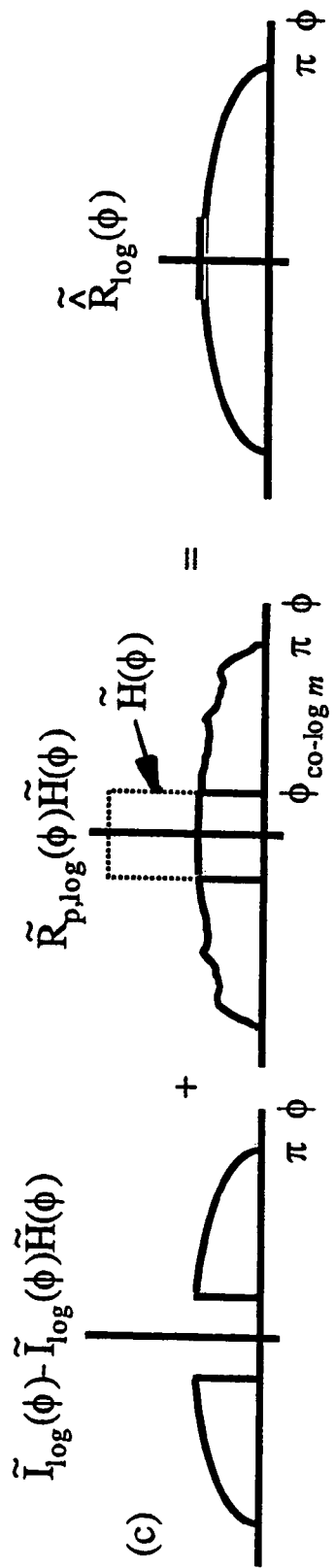

The goal of this invention is to compensate for atmospheric effects using only prior spatial information about the scene. The motivation for this was threefold. First, such an approach would likely work better than an atmospheric physics-based method when using airborne sensors since it is not dependent on the unknown state of the atmosphere above the sensor. Second, the repetitive and increasing amount of remote sensing data collected promises to eventually provide the needed prior surface reflectance information. Third, lightness algorithms that model the human visual system's ability to achieve color constancy over varying illumination conditions (multiplicative noise only) through spatial processing helped to inspire this effort to develop related algorithms for remote sensing applications.

This is the first development of a new class of algorithms that use prior surface reflectance information to correct for multiplicative and additive noise introduced by variations in illumination and atmospheric effects. They are called Surface Prior Information Reflectance Estimation (SPIRE) algorithms. The "Spatial SPIRE" algorithms employ spatial prior information and spatial processing, and explores the utility of prior spectral information. The ELM algorithm also uses spatial information about the scene in the form of pixel locations where ground truth spectra exist, but this is information about the current scene, and not prior information. Spatial SPIRE algorithms differ from ELM in that they utilize the low frequency spatial information applicable to each spectral channel for an entire image instead of focusing on specific pixels that may change between images.

Since they make no assumptions about the illumination or atmospheric conditions, SPIRE algorithms work under cloudy and artificial lighting conditions where physics-based codes may not. Also, unlike ELM, SPIRE algorithms do not require ground truth spectra at specific locations.

The prior spatial information needed by SPIRE can come from various sources, such as pre-existing reflectance maps or simulations. However, the most practical source of prior information is previous surface reflectance estimates made using either ELM or a physics-based code. Therefore, Spatial SPIRE algorithms do not always replace ELM or physics-based atmospheric compensation algorithms, but rather leverage their outputs obtained under ideal conditions in order to extend atmospheric compensation capabilities into non-ideal conditions.

The operational use of Spatial SPIRE algorithms would normally begin with the collection of an initial image under the best possible conditions in order to estimate reflectance using a physics-based code or, if ground truth spectra are available, ELM. If a physics-based code is used, then a hyperspectral sensor on board a satellite could, for example, repeatedly update a prior reflectance cube on clear days. This cube then can serve as the reference from which changes can be measured from aircraft or spacecraft.

Once this prior information is in place, subsequent single or multi-channel images can be processed using SPIRE algorithms, independent of cloud cover or the availability of ground truth spectra. Seasonal and precipitation-induced reflectance changes may be handled using different priors for different seasons and wet/dry/snow conditions whose selection is driven by ancillary information such as local weather data. For this paper, it is assumed that a recent prior was generated from an image collected under similar seasonal and precipitation conditions.

Our goal of this invention is to estimate local surface spectral reflectance changes using multiple observations under varying multiplicative and additive noise. We make the following assumptions:

1) The first observation, or group of observations, has been processed to estimate the surface reflectance. This is the prior.

2) Any changes or new objects in the scene occupy relatively few pixels and have defined edges, thereby modifying primarily the high spatial frequency content of the image.

3) The spatial frequency content of the multiplicative and additive illumination noises across the scene are band-limited to lower spatial frequencies that do not overlap those characterizing the reflectance changes to be estimated. There is no constraint on the frequency content of the image reflectance itself.

The sensed image, after any changes have occurred, is characterized at each spatial position $n_x$, $n_y$ and each wavelength $n_\lambda$ by:

$$i = rm + a \quad (1)$$

where i is the sensed image, r is the current surface reflectance and signal of interest, m is the multiplicative noise, and a is the additive noise. Each of these four terms is a three-dimensional array (often referred to as an image "cube") where $n_x$ and $n_y$ are spatial dimension indices and $n_\lambda$ is the spectral dimension index. All data are assumed to be discrete in space and wavelength.

Our problem is to estimate r given the sensed image i and the prior reflectance $r_p$. We first develop a solution for multiplicative noise when backscattering into the sensor is negligible so that additive noise is zero. We then develop the general solution for combined multiplicative and additive noise.

In this case, the additive noise a is zero but we have a multiplicative noise m varying spatially across the scene so that:

$$i = rm \quad (2)$$

We first move to log space to linearize the problem:

$$\log i = \log r + \log m \quad (3)$$

In (3), log m is confined to low spatial frequencies, while log r can have broad frequency support. We eliminate the low-frequency components of log m by high-pass filtering, which is equivalent to subtracting a spatially low-pass filtered version of the sensed image (h*log i, where * denotes convolution) from itself, where the filter h has support over the same nominal bandwidth as log m:

$$\log i - h*\log i = \log r - h*\log r + \log m - h*\log m \approx \log r - h*\log r \quad (4)$$

This operation approximately cancels the low frequency noise term log m, but also eliminates any low frequency components of log r (i.e. h*log r). Assuming any scene changes have negligible low-frequency content, we can recover these lost low-frequency components of log r by adding back a low-pass filtered version of the prior image to both sides:

$$\log \hat{r} = \log r - h*\log r + h*\log r_p = \log i - h*\log i + h*\log r_p \quad (5)$$

We then take the exponential, resulting in:

$$\hat{r} = \exp(\log i - h*\log i + h*\log r_p) \quad (6)$$

To illustrate this processing, we take the Discrete Time Fourier Transform (DTFT) (Oppenheim, et al., 1997; 1999) of the log of (6) to obtain, in which tildes denote transforms as a function of spatial frequency $\phi$, the subscript $_{log}$ denotes that the term is the DTFT of the log of the variable, and $\phi = [\phi_x, \phi_y]$:

$$\hat{R}^\%_{\log}(\phi) = I^\%_{\log}(\phi) - H^\%(\phi)I^\%_{\log}(\phi) + H^\%(\phi)R^\%_{p,\log}(\phi) \quad (7)$$

FIG. 1 depicts a one-dimensional example of equation. In FIG. 1(a), the sensed image is shown as the sum (in log space) of the reflectance $$R^\%_{\log}(\phi)$$

and the multiplicative noise $$M^\%_{\log}(\phi),$$

which is band limited to frequencies below the cut-off frequency $\phi_{co\text{-}log\ m}$. In FIG. 1(b), the log of the sensed image is high-pass filtered by subtracting a low-pass filtered version of itself. In FIG. 1(c), the missing low frequencies of the reflectance are restored using the low frequency content of the log of the prior, with a small difference due to the effect of any changes in the image. Note that high-frequency differences between the prior reflectance and the new reflectance are preserved and do not affect the processing. The specific cut-off frequency $\phi_{co\text{-}log\ m}$ used is application dependent and is selected based on the spectral content of $$M^\%_{\log}(\phi)$$

and the changes in $$R^\%_{\log}(\phi).$$

Figure 2:
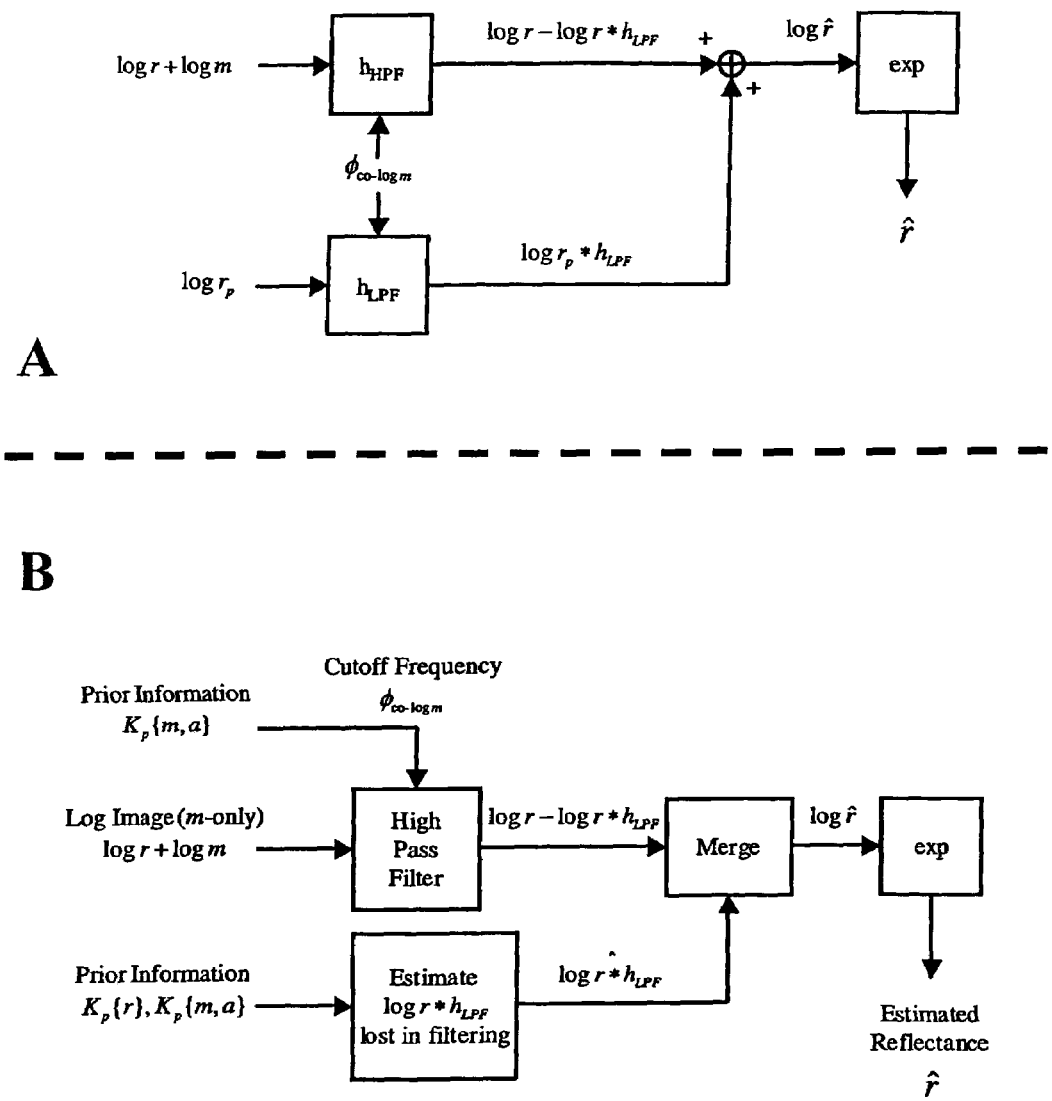
FIG. 2. (a) Multiplicative-noise-only spatial SPIRE algorithm tested and (b) the generalized processing block diagram. The high-pass-filtered log image is merged with an estimate of the lost low frequency components of the original log image derived from the prior. The exponential is then taken to estimate reflectance.

FIG. 2(a) depicts the corresponding processing block diagram. FIG. 2(b) depicts a more generic block diagram that accommodates other approaches to low-pass filtering and merging the high-passed image with the estimate of log $r*h_{LPF}$.

We now solve the more general problem with both spatially varying multiplicative noise and spatially varying additive noise across the scene where:

$$i = rm + a \quad (8)$$

We first remove the additive noise by subtracting a low-pass-filtered version of the image from itself, since a is limited to lower spatial frequencies. The low-pass filter used at this stage is designated $h_1$. This eliminates the additive noise at the expense of subtracting the term $h_1*(rm)$, a low-pass filtered version of the reflectance times the multiplicative noise, yielding:

$$i - h_1 * i = rm + a - h_1 * (rm + a) = rm - h_1 * (rm) \quad (9)$$

We next estimate the two-dimensional filtered function $h_1*rm$ by representing it as a sum of weighted orthogonal basis functions. For this research, the Discrete Cosine Transform (DCT) (Lim, 1990) was used; other possibilities exist, such as Lapped Orthogonal Transforms (LOT) (Malvar, 1992). We express the estimate of $h_1*(rm)$ as a DCT as follows:

$$est(h_1 * (rm)) = \begin{cases} \frac{1}{N_x N_y} \sum_{k_x=0}^{N_x-1} \sum_{k_y=0}^{N_y-1} w_x(k_x) w_y(k_y) C_E(k_x, k_y) \\ \cos\frac{\pi}{2N_x} k_x (2n_x + 1) \cos\frac{\pi}{2N_y} k_y (2n_y + 1), \quad \text{for } 0 \le n_x \le N_x - 1, 0 \le n_y \le N_y - 1 \\ 0, \quad \text{otherwise} \end{cases} \quad (10)$$

where:

$$w_i(k_i) = \begin{cases} \frac{1}{2}, & k_i = 0 \\ 1, & 1 \le k_i \le N_i - 1 \end{cases} \quad (11)$$

and $N_x$ and $N_y$ are the spatial dimensions of the image.

We find the weighting coefficient $C_E(k_x, k_y)$ for each basis function by setting all of the coefficients to zero and then estimating them one at a time starting with the lowest frequency terms, thus incrementally building an estimate of $h_1*rm$. For each coefficient we 1) step through the range of possible values for it, 2) estimate $h_1*rm$ using this and previously found coefficients, and then 3) estimate the reflectance using the multiplicative-noise-only algorithm of FIG. 2(a). The final value selected for each coefficient is the one that minimizes the mean square error (MSE) between the prior reflectance and the estimated reflectance.

The estimate $\hat{r}$ of the surface reflectance associated with the $est(rm*h_1)$ that minimizes the mean square error between $\hat{r}$ and $r_p$ can then be written in the form of the solution to the multiplicative-noise-only problem. A second low-pass filter $h_2$ (equivalent to h in the multiplicative-noise-only algorithm) is used in the log domain, and is given by:

$$\hat{r} = \exp\left( \frac{\log(i - h_1 * i + est(h_1 * (rm)))}{-h_2 * \log(i - h_1 * i + est(h_1 * (rm))) + h_2 * \log r_p} \right) \quad (12)$$

Figure 3:
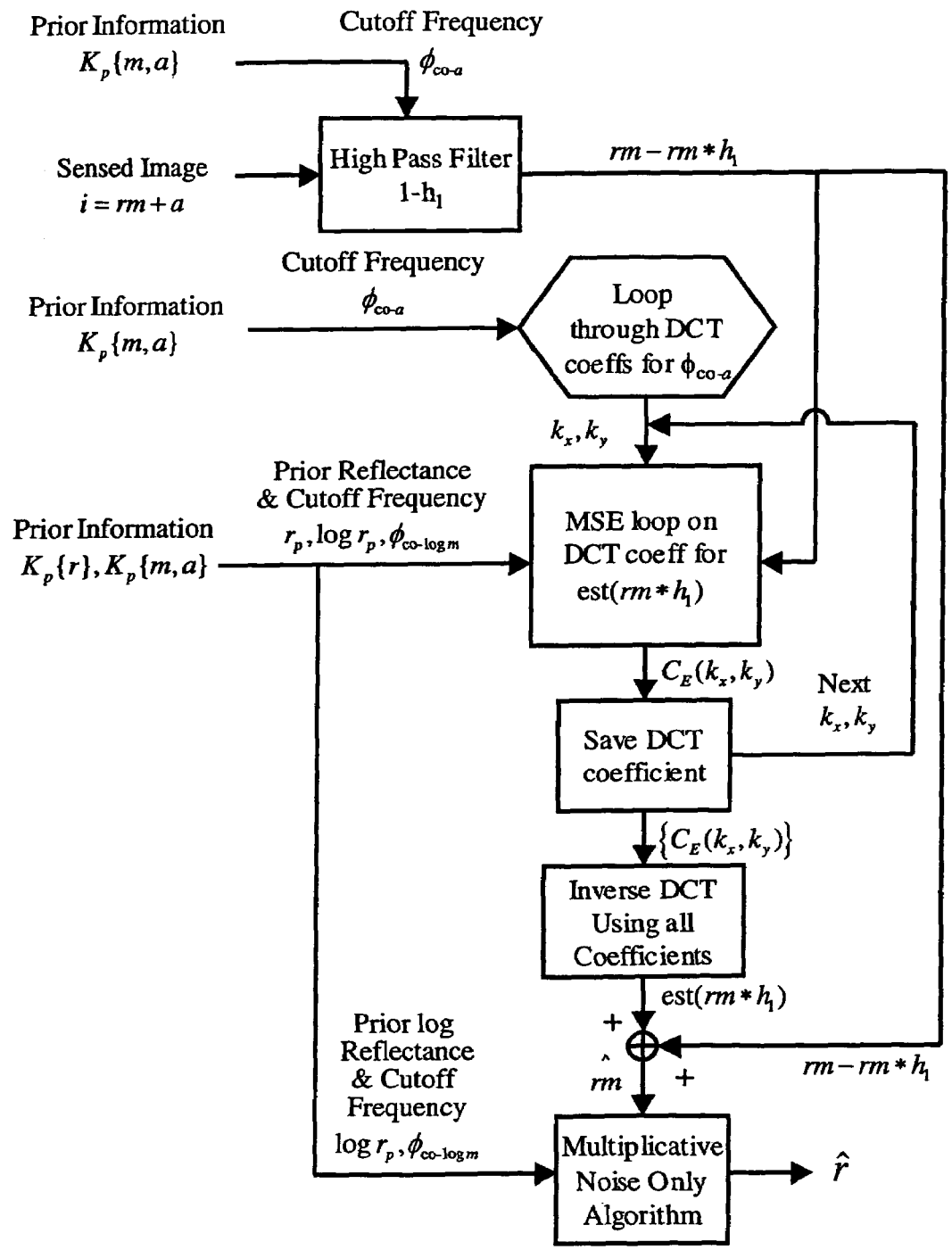
FIG. 3. Spatial SPIRE algorithm processing block diagram for multiplicative and additive noise. The sensed image is first high-pass filtered to remove the additive noise a. A loop is then entered to estimate the rm*$h_1$ lost using a Discrete Cosine Transform (DCT). The number of DCT coefficients needed is derived from the band limit $\phi_{co-a}$. For each DCT coefficient, a mean-square-error minimization loop estimates the correct value. The estimate of rm*$h_1$ is then added and the multiplicative-noise-only algorithm obtains the final estimated reflectance.

FIG. 3 depicts the processing flow diagram for this algorithm. Since $est(rm*h_1)$ is restricted to lower spatial frequencies, only those DCT coefficients passed by $h_1$ need be used in the estimate.

Various simplifications can be made to the algorithms described above if either the multiplicative or additive illumination noises are zero. The resulting algorithms are significantly more efficient computationally than the algorithms developed above. They experience performance degradation if the noise assumed to be spatially uniform is actually varying.

For example, in the multiplicative-noise-only case, if the noise is uniform (a random additive constant), then only the zero-frequency component (the mean) must be filtered from the log image and restored from the log prior. Similarly, if both the multiplicative and additive noises are spatially uniform, then only mean and variance statistics of the image and prior are required to solve the problem without any iteration. Finally, in most remote sensing applications, the additive noise can be assumed to be uniform while the multiplicative must be treated as varying. For such cases, the multiplicative and additive noise algorithm described in Section C can be simplified by estimating only the mean of rm in each channel image.

TABLE 1

Herbert Viggh

| Run | Date | Time (Local) | Altitude |
|---|---|---|---|
| 07 | Jun. 24, 1997 | 12:26–12:28 | 6,087' |
| 13 | Jun. 24, 1997 | 13:13–13:16 | 11,433' |
| 26 | Jun. 24, 1997 | 14:24–14:27 | 11,410' |
| 06 | Jun. 26, 1997 | 11:43–11:46 | 5,994' |
| 22 | Jun. 27, 1997 | 07:37–07:39 | 6,077' |
| 31 | Jun. 27, 1997 | 08:19–08:22 | 11,333' |

TABLE 2

Herbert Viggh

| Channels | Reason Removed |
|---|---|
| 1–6 | Negative pixel values |
| 19 | Striping |
| 58–79 | H2O vapor absorption |
| 82–92 | H2O vapor absorption |
| 100–117 | H2O vapor absorption |
| 130–154 | H2O vapor absorption |
| 155–170 | Negative pixel values |
| 173–205 | Negative pixel values |
| 206–210 | H2O vapor absorption |

Spatial SPIRE algorithms are suitable for single channel, multispectral, and hyperspectral data, since all can be processed one channel at a time. In order to compare SPIRE algorithm performance to a state-of-the-art physics-based atmospheric compensation algorithm, hyperspectral remote sensing data was used since it is required by physics-based codes. The Department of Energy (DOE) operates the Southern Great Plains Site (SGPS) Atmospheric Radiation Measurement (ARM) and Cloud and Radiation Testbed (CART) facility located southeast of Lammont, Okla. HYDICE airborne hyperspectral sensor data (Basedow, et al., 1995) was collected during 23 to 28 Jun. 1997 as part of the Atmospheric Ompensaiton Investigation (ACI) data collection (Lockheed-Martin, 1997). The ACI over the ARM Site was collected to provide hyperspectral data for the development and testing of atmospheric compensation algorithms. Various test panels were in place on the ground, and ground truth data was collected over these panels using a spectroradiometer. Various other instruments were used to measure meteorological conditions, including all-sky photographs.

With this data Spatial SPIRE algorithms were compared to the ELM and ATREM atmospheric compensation algorithms. Six HYDICE runs were selected from three different days of the ARM Site data collect. Since pixels of known reflectance are typically not available under operational conditions, this comparison is mainly aimed at comparing SPIRE to ATREM, with ELM used as a ground-truth baseline. While SPIRE can work under conditions that ATREM cannot (single or multiple channels, overcast conditions above sensor), the authors felt it important to compare the Spatial SPIRE algorithm performance to that of an established technique known to the community.

Table 1 shows the times and altitudes of the six runs over the ARM Site, all of which contain calibrated test panels. Morning, noon, and mid-afternoon runs were made, which introduced shadows and varying solar illumination angles. The different altitudes of the runs introduced image scale differences up to a factor of two. Also, the flight paths differed so that the images were rotated with respect to each other. In addition, the truck carrying the spectroradiometer appeared in different locations in each run, which introduced small changes from the prior, making this a suitable dataset on which to test SPIRE algorithms. Although the truck was not selected as a test pixel due to its non-uniformity, the mowed grass exposed when the truck was moved served as a "modified" test pixel. Some runs contained shadows due to low sun angle, which are high-spatial frequency illumination changes that could affect reflectance estimates in non-shadowed areas.

ELM processing requires known spectra for selected pixels in the image. Ground truth measurements of spectra over test panels were available for the ARM Site data. Ground truth spectra for the 2-percent and 64-percent reflectivity panels, collected on 24 Jun. 1997, were used to perform the ELM calibration. Sub-image cubes (sub-cubes) similar in spatial extent to the image in FIG. 4 were extracted from the original full-size radiance cubes and were preprocessed to remove artifacts involving integer wrapping of some bright pixels into negative numbers. For each calibration panel, all interior pixels were selected and input to ENVI's Empirical Line Calibration (ELM) routine, which performs a linear regression to minimize the effects of noise across the uniform panels (ENVI User's Guide, 1997). The sub-cubes for all six runs were processed to estimate reflectance. The 137 channels most affected by water vapor absorption and negative radiance values were removed leaving a total of 73 spectral channels, as shown in Table 2.

ATREM Version 3.0 was used to estimate reflectance from each of the six run cubes. For each run, the entire image cube (full spatial extent) was processed with all 210 original HYDICE sensor channels included. All six runs were processed using the same ATREM atmospheric input parameters ((ATREM) User Guide, 1997) as follows: The three channel center wavelengths (microns) and the number (n) of sub-bands averaged in each atmospheric window within the 0.94-µm water vapor band were: 0.8650 (3) 1.030 (3) 0.940 (7). For the 1.14-µm water vapor band the following parameters were used: 1.050 (3) 1.235 (3) 1.1375 (7). The mid-latitude summer atmospheric model was used. Water vapor, carbon dioxide, ozone, nitrous dioxide, carbon monoxide, methane, and oxygen were included in the atmospheric gaseous transmission calculations. A total column ozone value of 0.34 atm-cm was assumed. The continental aerosol model was used with a visibility of 23 km.

After the estimated reflectance cubes were generated, sub-cubes matching the same spatial area of the ELM sub-cubes were extracted, and the channels affected by water vapor absorption and negative radiance values were removed leaving 73 channels.

Spatial SPIRE processing was performed on the same sub-cubes used for the ELM processing. It was seen that both additive and multiplicative effects were essentially spatially uniform by registering the ELM images from different days and measuring differences between them. Therefore, a simplified version of the multiplicative and additive SPIRE algorithm was used that assumes the additive noise is uniform so that only the mean of each channel image is removed and only the mean of rm needs to be estimated in each channel.

A full-size reflectance cube generated using ELM from the original full-size Run 07 radiance cube provided the prior information. This cube was warped to generate five full-size prior cubes registered to each of the five radiance sub-cubes for runs 13, 26, 06, 22, and 31. ENVI's image-to-image warping routine using hand-selected ground control points and the RST (Rotation, Scaling, and Translation) warping method with nearest neighbor re-sampling was employed to do the warping. Sub-cubes were then cut from each warped full-size prior cube, covering the same pixel ranges as the sub-cube for that run.

We treat the ELM results as ground truth, and measure the variance and mean error between the six ELM estimates and the six estimates from ATREM and Spatial SPIRE, where each estimate is based on the same set of 19 test pixels.

Figure 4:
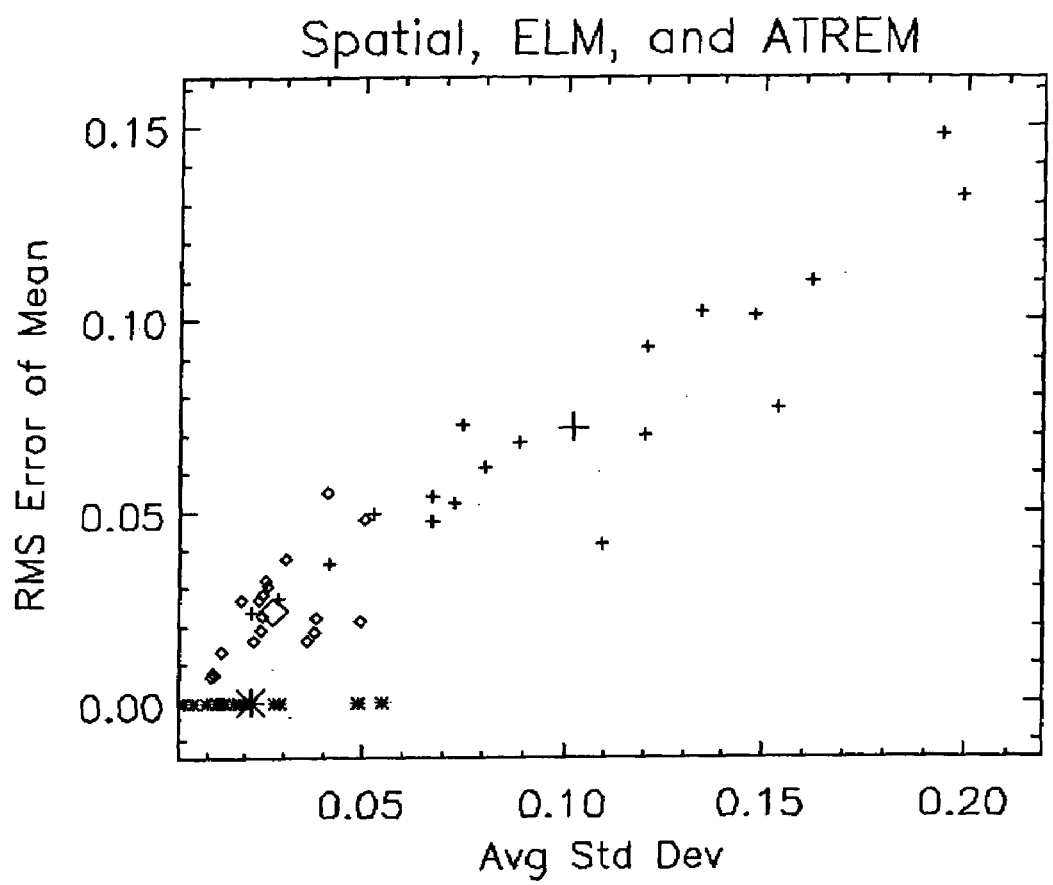
FIG. 4. Scatter plot of mean and standard deviation performance of spatial SPIRE (diamonds), ELM (*), and ATREM (+) for estimation of surface spectral reflectance for all 19 pixel types. The horizontal axis represents the average standard deviation over all 73 spectral channels, where the standard deviation in each channel was calculated over the reflectance estimates of all six runs (Runs 06, 07, 13, 22, 26, and 31). The vertical axis is the RMS error over all spectral channels for the mean reflectance estimate minus the mean reflectance estimate of ELM as ground truth, which is why ELM has zero RMS error. The larger symbols represent the mean of the points plotted with that symbol. We see that spatial SPIRE has better standard deviation and RMS performance than ATREM.

FIG. 4 shows the relation between the mean and standard deviation of Spatial SPIRE, ELM, and ATREM when estimating surface spectral reflectance for 19 types of pixels. Many of these pixels were from uniform materials such as panels, while others were from mottled materials such as grass and road for which the reflectance estimates may vary due to small registration errors.

The horizontal axis in FIG. 4 represents the average standard deviation over all spectral channels, where the reflectance standard deviation in each channel was calculated over all six runs. The vertical axis is the root-mean-square (RMS) difference (error) between the mean reflectance estimates for ELM serving as ground truth, and the estimates of SPIRE and ATREM, which is why ELM has zero RMS error; these errors are computed over all spectral channels. In general, Spatial SPIRE has better mean and standard deviation performance than ATREM and about the same standard deviation performance as ELM.

Figure 5:
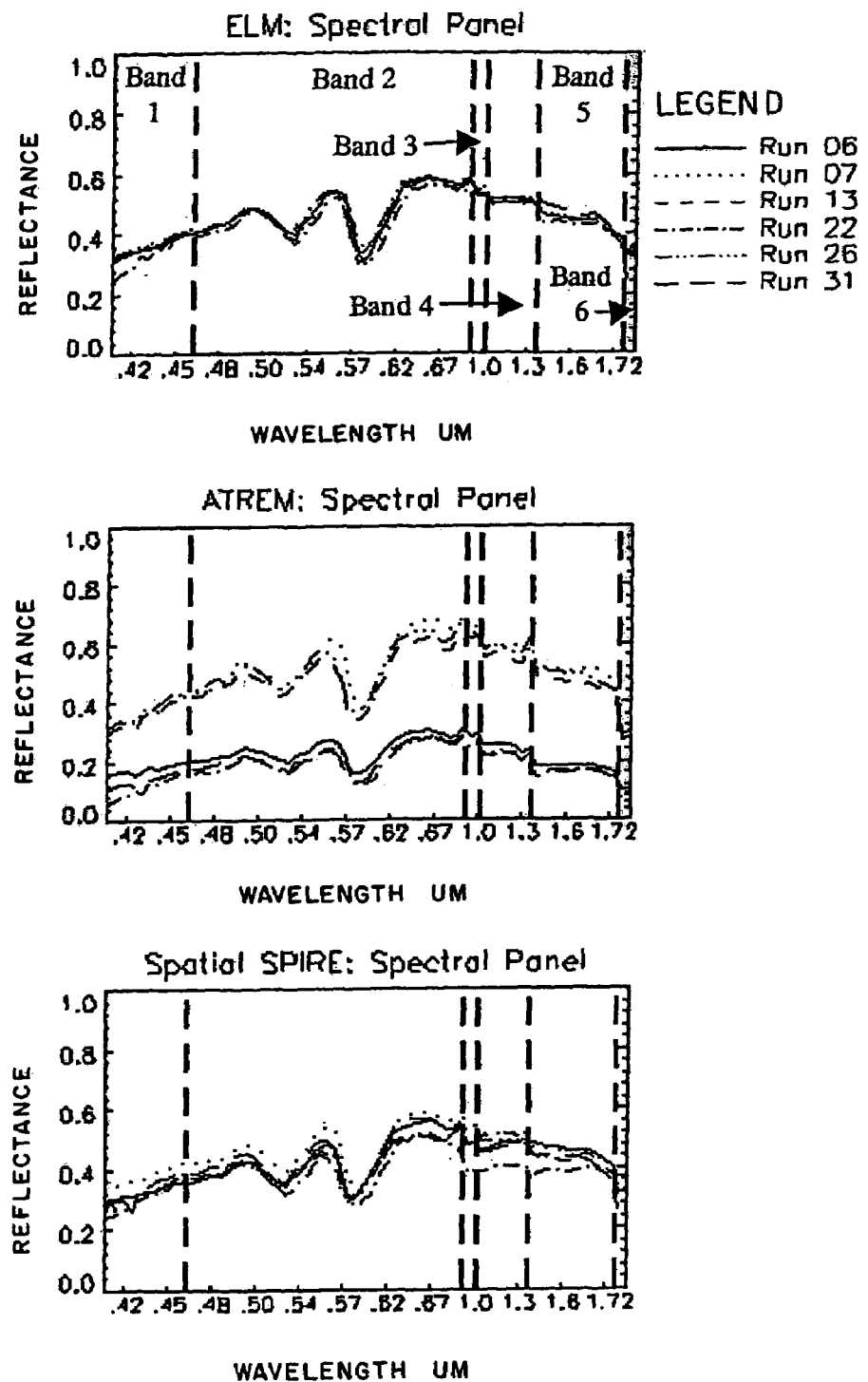
FIG. 5(a) and (b). ELM, ATREM, and Spatial SPIRE spectral reflectance estimates for all six runs for a single pixel on the spectral panel (a) and mowed grass (b). There are six bands of contiguous channels left after dropping problem channels, defined as Bands 1-6 as depicted in the upper left plot of the spectral panel reflectance.
FIG. 5(c) and (d). ELM, ATREM, and Spatial SPIRE spectral reflectance estimates for all six runs for the modified pixel (c) and the 2 percent panel (d). Spatial SPIRE's poor performance at longer wavelengths on the 2 percent panel is due to errors in estimating the additive noise a under low SNR conditions.
Figure 5:
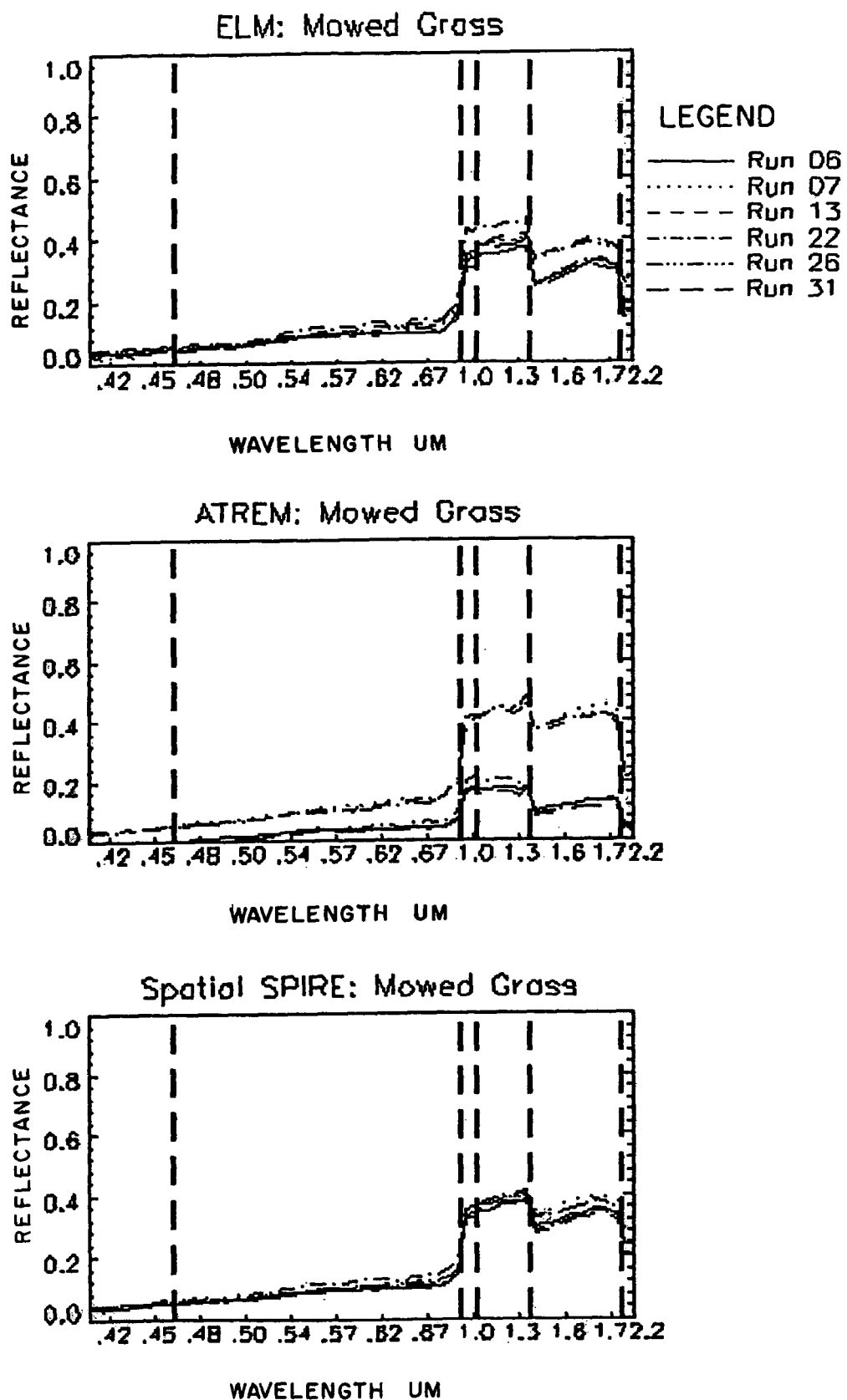
Figure 5:
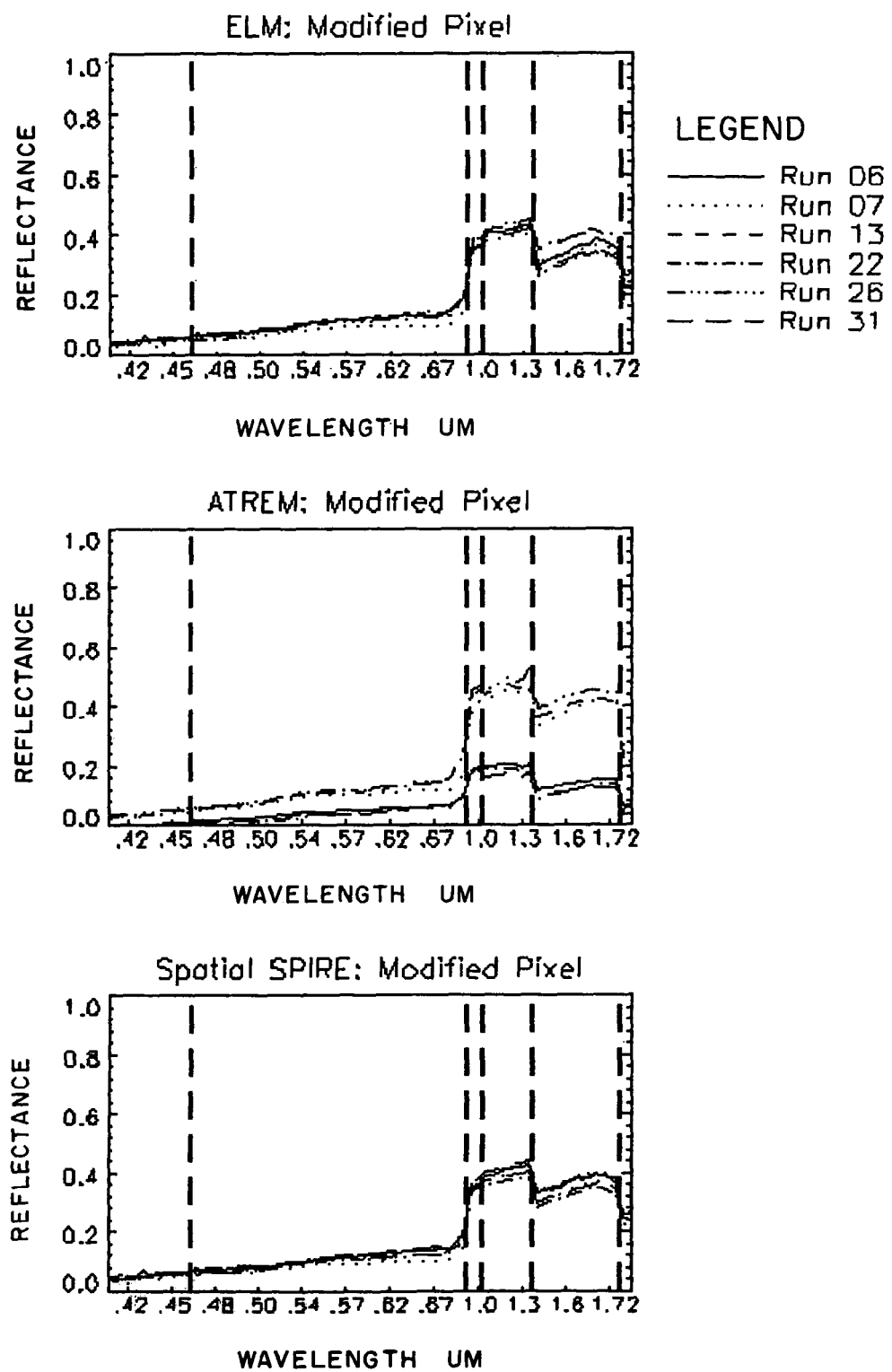
Figure 5:
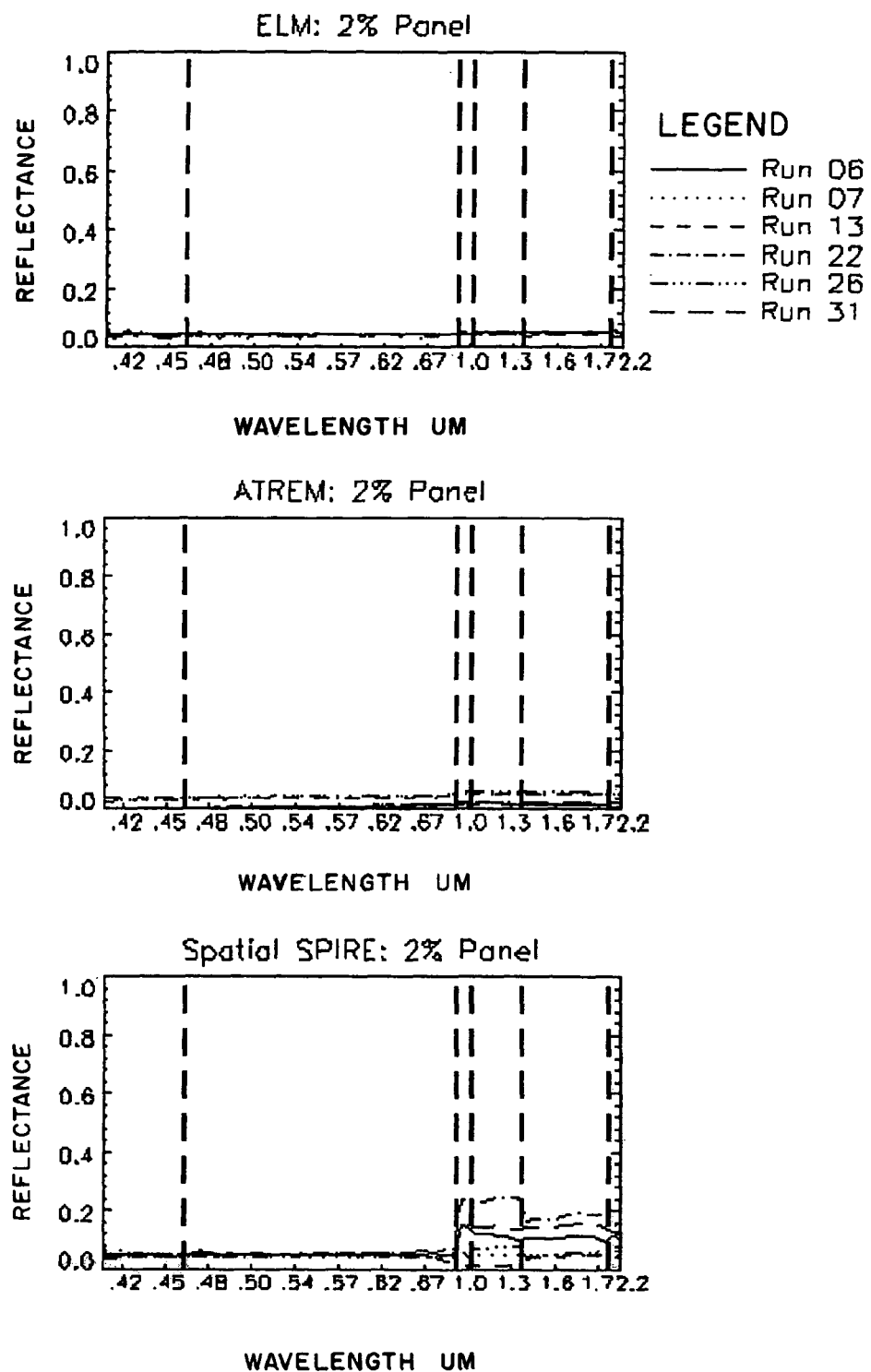

FIG. 5 (a)-(d) shows the estimated reflectance spectra generated by the ELM, ATREM, and Spatial SPIRE algorithms for four of the nineteen different types of pixels. In each plot, five vertical dashed lines are drawn where one or more channels were removed due to water absorption and other effects. The bands of channels between the vertical lines will be referred to as Bands 1-6, as denoted in FIG. 5(a) for the spectral panel.

FIG. 5(a) depicts the results for the spectral panel, which provides several sharp absorption features at known wavelengths. FIG. 5(b) shows that the Spatial SPIRE reflectance estimates for mowed grass agree much better with ELM than do the ATREM results. If we consider ELM as ground truth, then Spatial SPIRE consistently performs better than ATREM. Similar results to ATREM were obtained when the same runs were processed using the AFRL/MODTRAN code. The ATREM estimates tend to group into two clusters because three runs were collected under clear skies, but three runs had high clouds or haze. Clouds and haze produce the lower ATREM reflectance estimates due to the reduced illumination reaching the ground. This illustrates the problems physics-based codes can have with overcast clouds, which do not affect the SPIRE algorithms. Similar problems with ATREM were noted in (Sanders, et al., 1998).

FIG. 5(c) depicts a pixel where a truck was present in the Run 07 image used to generate the priors, but which moved and exposed mowed grass in its place. This is the "modified" pixel. By comparing this mowed grass pixel to the one in FIG. 5(b), we see that Spatial SPIRE estimated the new reflectance of this pixel quite well.

FIG. 5(d) depicts a 2-percent reflectivity calibration panel. While there is excellent agreement between ELM and Spatial SPIRE in Bands 1 and 2, Spatial SPIRE has high variance in Bands 3-6 due to low signal levels. For pixels with higher reflectance, this is not true. This excessive variance in the Spatial SPIRE results is due to errors in estimating the mean value of rm to restore after removing the additive noise a. These errors disproportionately affect low signal values since in log space they have a larger percentage effect on a low reflectivity material than a higher one. In channels with very low signal-to-noise ratio (SNR), prior noise will also have a large effect on the log of the prior reflectance as well. These two effects combine to create the large errors seen in the longer wavelength channels for low reflectivity materials.

Many hyperspectral classification applications involve a human analyst who identifies known or interesting pixels in the image. These pixels then train an algorithm to classify other pixels. Such supervised classifiers are often applied only to the strongest Principal Components in order to limit the dimensionality of the problem. Classification accuracy often suffers when the illumination varies between and within the training image and the image of interest. Classification performance is improved when the estimated reflectance images properly compensate for illumination variations between and within scenes.

Supervised classification experiments were run on the reflectance cubes estimated by the ELM, ATREM, and Spatial SPIRE algorithms. For each type of reflectance image cube, a Principal Components Analysis was performed on the cube for Run 07, and the resulting Principal Component (PC) rotation for the 20 most significant PCs was applied to the other five cubes. Training pixels were then collected from the Run 07 cube that corresponded to the 19 test pixel types. For each pixel type, or class, only a single training pixel was used since they were quite representative. ENVI's minimum distance classifier was then trained using the 19 pixel classes and applied to all six test image cubes of each type.

FIG. 7 shows typical classification results, exemplified by the results for Run 13(a) and Run 06(b). Run 13 was collected on the same day as the training data from Run 07 under similar illumination conditions, so classification performance is good for all three algorithms. The Run 06 data was collected on a different day with different illumination conditions. The performance was poor for ATREM due to thin overhead clouds, while Spatial SPIRE performance is possibly superior to even ELM (for example, note the mowed grass). This demonstrates Spatial SPIRE's advantages relative to physics-based codes and the utility of SPIRE reflectance estimates in downstream processing applications such as pixel classification.

A new class of algorithms has been developed to estimate the spectral reflectance of local changes under spatially and spectrally varying multiplicative and additive noise. Rather than modeling the physics of the atmosphere and illumination to compensate for these effects, or using known ground truth spectra in the image, prior information about low spatial frequency content in each spectral channel is used instead. Algorithms were developed for both the multiplicative-noise-only problem and for problems with both multiplicative and additive noise.

The Spatial SPIRE algorithm for multiplicative and additive noise was compared to existing ATREM and ELM atmospheric compensation algorithms using HYDICE ARM Site hyperspectral data. Spatial SPIRE algorithm performance was found to be nearly identical to the ELM ground-truth based results, better than ATREM overall, and significantly better than ATREM under high clouds and haze.

Spatial SPIRE algorithms offer a robust technique for estimating the spectral reflectance of localized sets of pixels in remote sensing imagery under operational conditions where current techniques may fail. In addition, Spatial SPIRE algorithms can by used equally well with single channel, multispectral, or hyperspectral data. The utility of prior low-frequency spatial information when estimating reflectances using Spatial SPIRE algorithms might motivate the development of libraries of such information for operational use.

While the invention has been described in its presently preferred embodiment it is understood that the words which have been used are works of description rather than words of limitation and that changes within the purview of the appended claims may be made without departing from the scope and spirit of the invention in its broader aspects.

What is claimed is:

1. A process for measuring surface reflectance of an object of interest in a set of image data said process comprising the steps of:

collect the set of image data which contains the surface reflectance of the object of interest as well as additive noise caused by variations in illumination and an atmospheric effects set;

make an estimate of the additive noise in the set of image data;

process the image data in a high pass filter to remove the estimate of additive noise from the set of image data and getting thereby a processed image set;

use a Discrete Cosign Transform (DCT) on the processed image set to estimate an amount of image signal lost due to the atmospheric effects set;

add the estimate of image signal lost to the processed image set to get a sum reflectance estimate; and process the sum reflectance estimate with a multiplicative noise only algorithm to obtain thereby the surface reflectance of the object of interest.

2. A process, as defined in claim 1, wherein said collection step is performed using image sensors that detect image data in a form of pixel spectral vectors and which output an image (i)=rm where r equals the surface reflectance of the object of interest and m is a multiplicative noise spectrum.

3. A process, as defined in claim 2, wherein there are N channels of pixel spectral vectors {x} that are rotated into a log m principle component (PC) space to produce a rotated ensemble set {y}.

4. A process, as defined in claim 3, wherein image formation of the object of interest is elicited by performing a Hadamard product of the rotated ensemble set {y}.

* * * * *